(12) United States Patent
Bastia

(10) Patent No.: US 11,377,681 B2
(45) Date of Patent: Jul. 5, 2022

(54) METHOD FOR DETERMINING HELICOBACTER PYLORI

(71) Applicant: THD S.p.A., Reggio Emilia (IT)

(72) Inventor: Filippo Bastia, Modena (IT)

(73) Assignee: THD S.p.A., Correggio (IT)

( * ) Notice: Subject to any disclaimer, the term of this patent is extended or adjusted under 35 U.S.C. 154(b) by 318 days.

(21) Appl. No.: 16/075,425

(22) PCT Filed: Feb. 3, 2017

(86) PCT No.: PCT/IB2017/050611
§ 371 (c)(1),
(2) Date: Aug. 3, 2018

(87) PCT Pub. No.: WO2017/134627
PCT Pub. Date: Aug. 10, 2017

(65) Prior Publication Data
US 2019/0211381 A1     Jul. 11, 2019

(30) Foreign Application Priority Data
Feb. 5, 2016   (IT) .......................... 102016000011879

(51) Int. Cl.
| | |
|---|---|
| *C12Q 1/689* | (2018.01) |
| *C12Q 1/6827* | (2018.01) |
| *G01N 33/569* | (2006.01) |
| *C12Q 1/04* | (2006.01) |
| *C12Q 1/6806* | (2018.01) |
| *C12Q 1/686* | (2018.01) |

(52) U.S. Cl.
CPC ............. *C12Q 1/6827* (2013.01); *C12Q 1/04* (2013.01); *C12Q 1/6806* (2013.01); *C12Q 1/686* (2013.01); *C12Q 1/689* (2013.01); *G01N 33/569* (2013.01); *G01N 33/56922* (2013.01); *C12Q 2600/106* (2013.01); *C12Q 2600/156* (2013.01); *C12Q 2600/16* (2013.01); *C12Q 2600/166* (2013.01)

(58) Field of Classification Search
CPC ....................................................... C12Q 1/689
See application file for complete search history.

(56) References Cited

FOREIGN PATENT DOCUMENTS

| CN | 101665824 A | 3/2010 |
|---|---|---|
| WO | 00/29618 A1 | 5/2000 |
| WO | 2014/087055 A1 | 6/2014 |

OTHER PUBLICATIONS

Gazi, S et al. Annals of Gastroenterology 26:226-232. (Year: 2013).*

The Plant-Microbe Genomics Facility (PMGF) at the Ohio State University, "Procedures and Recommendations for Quantitative PCR", version 1.2, Apr. 2003. (Year: 2003).*

(Continued)

*Primary Examiner* — Diana B Johannsen
(74) *Attorney, Agent, or Firm* — Knobbe, Martens, Olson & Bear, LLP

(57) ABSTRACT

An in vitro method enables determination of the antibiotic resistance of *Helicobacter pylorifor* in a biological sample isolated from an individual. The method includes amplifying at least one portion of at least one gene of *Helicobacter pylori*. The at least one gene includes at least one mutation site responsible for resistance to an antibiotic. A kit can be used for performing the method.

7 Claims, 1 Drawing Sheet

Specification includes a Sequence Listing.

(56) References Cited

OTHER PUBLICATIONS

Goel, G. et al. Journal of Applied Microbiology 99:435-442. (Year: 2005).*

Furuta, Takahisa et al. 2007 "Modified allele-specific primer polymerase chain reaction method for analysis of susceptibility of Helicobacter pylori strains to clarithromycin" Journal of Gastroenterology and Hepatology 22: 1810-1815.

Nakamura, Akiko et al. 2007 "Determination of mutations of the 23S rRNA gene of Helicobacter pylori by allele specific primer-polymerase chain reaction method" Journal of Gastroenterology and Hepatology 22: 1057-1063.

Boyanova, Lyudmila et al. 2015 "Clarithromycin Resistance Mutations in Helicobacter pylori in Association with Virulence Factors and Antibiotic Susceptibility of the Strains" Microbial Drug Resistance 22: 227-232.

Scaletsky, Isabel C. A. et al. 2011 "Application of Real-Time PCR Stool Assay for Helicobacter pylori Detection and Clarithromycin Susceptibility Testing in Brazilian Children" Helicobacter 16: 311-315.

Li, Yuan et al. 2012 "Detection of clarithromycin resistance in Helicobacter pylori following noncryogenic storage of rapid urease tests for 30 days" Journal of Digestive Diseases 13: 54-59.

Shabereiter-Gurtner, C et al. 2004 "Novel Real-Time PCR Assay for Detection of Helicobacter pylori Infection and Simultaneous Clarithromycin Susceptibility Testing of Stool and Biopsy Specimens" Journal of Clinical Microbiology 42: 4512-4518.

International Search Report for International Application No. PCT/IB2017/050611 dated Jul. 3, 2017.

\* cited by examiner

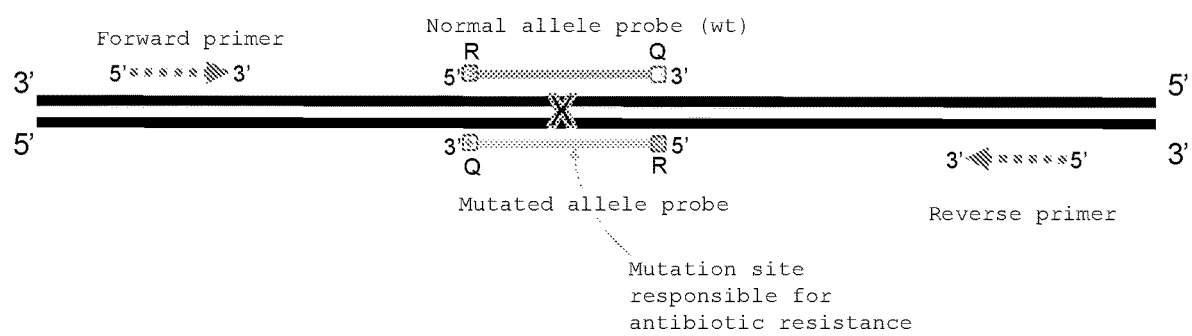

SEQUENCE LISTING

<160> NUMBER OF SEQ ID NOS: 24

<210> SEQ ID NO 1
<211> LENGTH: 641
<212> TYPE: DNA
<213> ORGANISM: Artificial Sequence
<220> FEATURE:
<223> OTHER INFORMATION: Portion of the 23S rRNA gene

<400> SEQUENCE: 1

```
acagcgatgt ggtctcagca aagagtccct cccgactgtt taccaaaaac acagcacttt      60
gccaactcgt aagaggaagt ataaggtgtg acgcctgccc ggtgctcgaa ggttaagagg     120
atgcgtcagt cgcaagatga agcgttgaat tgaagcccga gtaaacggcg ccgtaacta     180 taacggtcct aaggtagcga aattccttgt cggttaaata ccgacctgca tgaatggcga     240
acgagatggg agctgtctca accagagatt cagtgaaatt gtagtggagg tgaaaattcc     300
tcctacccgc ggcaagacgg aagagacccc gtggaccttt actacaactt agcactgcta     360
atgggaatat catgcgcagg ataggtggga ggctttgaag taagggcttt ggctcttatg     420
gagccatcct tgagatacca cccttgcatg tttctgttag ctaactggcc tgtgttatcc     480
caggcaggac aatgcttggt gggtagtttg actggggcgg tcgcctccta aaaagtaacg     540
gaggcttgca aaggttggct cattgcggtt ggaaatcgca agttgagtgt aatggcacaa     600
gccagcctga ctgtaagaca tacaagtcaa gcagagacga a                         641
```

<210> SEQ ID NO 2
<211> LENGTH: 212
<212> TYPE: DNA
<213> ORGANISM: Artificial Sequence
<220> FEATURE:
<223> OTHER INFORMATION: Portion of the 23S rRNA gene amplified

<400> SEQUENCE: 2

```
ttaaataccg acctgcatga atggcgaacg agatgggagc tgtctcaacc agagattcag      60
tgaaattgta gtggaggtga aaattcctcc tacccgcggc aagacggaaa gacccccgtgg    120 acctttacta caacttagca ctgctaatgg gaatatcatg cgcaggatag gtgggaggct     180
ttgaagtaag ggctttggct cttatggagc ca                                   212
```

<210> SEQ ID NO 3
<211> LENGTH: 2487
<212> TYPE: DNA
<213> ORGANISM: Artificial Sequence
<220> FEATURE:
<223> OTHER INFORMATION: Portion of the amplified normal gyrA gene

<400> SEQUENCE: 3

```
atgcaagatc atttagtcaa tgaaacaaaa aatattgtag aagtggggat tgattcttct    60
attgaagaga gctatttggc ttattccatg agcgtgatca tagggcgcgc tttaccggac   120
gctagagacg gcttaaagcc tgtgcatagg cgtattttgt atgcgatgca tgaattaggc   180
cttacttcca aagtcgctta taaaaaaagc gctaggatcg tgggtgatgt gattggtaaa   240
taccacccccc atggcgacac cgcagtttat gatgcgttag tgagaatggc gcaagatttt   300
tctatgcgct tggaattagt ggatgggcag ggcaactttg gctctattga tggcgataac   360
gccgcagcga tgcgttacac tgaagccaga atgaccaagg cgagtgaaga gattttaaga   420
gatattgata agacaccat tgattttgtg cctaattacg atgacacctt aaaagagcca   480
gatattttac caagccgtct gcctaaccttt ttagtcaatg gggctaatgg atcgccgta   540
gggatggcga cttctatccc ccctcatagg attgatgaaa tcatagacgc tttagcgcat   600
gtcttaggaa accctaacgc tgaattagat aaaattttgg aatttgtcaa aggacctgac   660
tttcctactg gtgggatcat ctatggcaag gcgggtattg ttgaagccta taaaacgggg   720
cgagggcgcg tgaaagtgcg ggccaaagtg catgtggaaa agacaaaaaa taaagaaatc   780
atcgttttag gtgaaatgcc ttttcaaacc aataaagcca aattagtgga acaaatcagc   840
gatttagcgc gagaaaaaca aattgaaggc attagcgaag tgcgcgatga agcgataga   900
gagggcatta gagtggtgat tgaattaaaa agagacgcga tgagtgaaat tgtcttaaac   960
caccttttaca aactcaccac tatggagacc acttttagca tcattttact cgctatttac  1020
aataaagagc ctaagatttt cacgctttta gagttgttgc gcctttttctt aaaccataga  1080
aagaccatta ttataagacg cacgattttt gaattagaaa aggctaaggc cagagcgcat  1140
attttagagg gctatttgat cgccttggac aatattgatg aaatcgtgcg actcattaaa  1200
acaagcccaa gcccagaagc ggctaaaaac gccttaatag agcgttttag tttgagcgag  1260
atccaaagca aagccatttt agaaatgcgt ttgcaacgct tgacaggcct tgaaagagat  1320
aagatcaaag aagaatacca aaacttatta gagcttattg atgatctcaa tggcatttta  1380
aagagcgaag atcgcttgaa tgaagtcgtc aaaacagagc ttttagaagt caaagagcag  1440
ttttcttctc caaggcgcac tgaaattcaa gaatcttatg aaagtattga tacagaagat  1500
ttgatcgcta atgagcctat ggtagtgagc atgagctata aggctatgt gaaaagagtg  1560
gatttaaaag cctatgaaag gcaaaatcgt ggcggtaaag gcaagctttc aggcagcact  1620
tatgaagatg atttcattga aaacttttttt gtggctaaca cgcatgatat tttgctcttt  1680
atcaccaata aggggcaatt gtatcatttg aaagtctata aaatcccaga agcgagccgg  1740
atcgctatgg gtaaagctat tgtgaattta atctcactcg ctcctaatga aaagatcatg  1800
gcaaccctaa gcactaaaga ttttagcgat gaacgctctt tagctttctt cacgaaaaat  1860
ggcgtggtga agcgcaccaa tttgagcgaa tttggcggta ataggagtta tagcggtatc  1920
agagcgattg ttttagatga aggcgatgaa ttagtgggcg caaagttgt ggataaaaac  1980
gctaagcatt tgctcatcgc atcttatttg gcatgttca ttaaattccc tttagaagac  2040
gtgcgcgaaa taggaagaac tactcgtggg gttatgggta ttagactgaa tgaaatgat  2100
tttgttgtcg cgcggttgt cattagcgat gatagcaaca agcttttgag cgtgagcgag  2160
aacgggcttg gcaagcaaac tctagccgaa gcgtatagag agcaatctcg tggaggtaag  2220
```

```
ggggtcattg gcatgaagct cactcaaaag accggtaatt tggtgagcgt tatcagcgtg    2280
gatgatgaga acctgaattt gatgatcctt accgcgagcg cgaaaatgat tagagtttcc    2340
attaaagata ttagagaaac cggaagaaat gccagtgggg taaaactcat aaacaccgct    2400
gataaagtcg tgtatgtcaa ttcttgccct aaagaagaag agccagaaaa tttagaaacc    2460
tcttcggtgc aaaatttgtt tgagtga                                        2487
```

<210> SEQ ID NO 4
<211> LENGTH: 1980
<212> TYPE: DNA
<213> ORGANISM: Artificial Sequence
<220> FEATURE:
<223> OTHER INFORMATION: Portion of the amplified normal pbp-1 gene

<400> SEQUENCE: 4

```
atgctaaaaa agatttttta tggttttatc gttttatttt tgattgtcat agggttgtta      60
gccattctta tcgctcaagt ttgggtaact acggataagg atattgctaa aattaaagat     120
tatcgcccgg gagtcgcttc acagatttta gaccgaaaag ggcgtttgat cgccaatatc     180
tatgataaag aattccgttt ttatgcgcgt tttgaagaaa tcccccccacg atttattgaa     240 agccttttag cggtagaaga cccctctctt tttgagcatg ggggatcaa tttagacgct     300 atcatgcgcg ctatgattaa aaacgctaaa agcggtcgct acactgaagg gggtagcacc     360
ctaacccaac aactcgttaa aaacatggtg ctcacgcgca aaaaaccct aaccagaaaa     420 ctcaaagaag ctatcatttc catacgcatt gaaaaagtct aagcaaaga gaaaatttta     480 gagcgttatt tgaaccaaac ttttttttggg catgggtatt atggcgtgaa accgcaagc     540 ttagggtatt ttaaaaaacc ccttgacaaa ctcacgctta agaaatcac catgttagtc     600 gccttgccta gggctccgag tttttatgat cctaccaaaa atttagaatt ttcactctct     660
agggctaatg atatttaag gcggttgtat tctttaggct ggatttcttc taacgagctc     720
aaaggcgctc tcaatgaagt gccaatcgtc tataaccaaa cttccacgca aaatatcgct     780
ccctatgtcg tggatgaagt gttgaagcaa ttggatcaat tagatgggtt aaaaaacccaa    840 ggctatacca taaagctcac gatagatttg gattaccaac gcttagcgtt agagtccttg     900
cgttttgggt atcaaaaaat cttagaaaaa atcgctaaag aaaagccaaa actaacgca     960 tctaacgaaa atgaagacaa tttgaacgct agcatgatcg ttacagacac gagcaccggt    1020
aagattttag ctttagtggg ggggattgat tataaaaaaa gcgctttcaa tcgcgccacg    1080
caagccaaac ggcagtttgg gagcgcgata aagcctttttg tgtatcaaat cgcttttgat    1140
aatggctatt ccaccacttc taaaatccct gatactgcgc gaaattttga aaatggcaat    1200
tatagtaaaa acagcgaaca aaaccacgca tggcatccca gcaattattc tcgcaagttt    1260
ttagggcttg taaccttgca agaagccttg agccattcgt taaatctagc cacgatcaat    1320
ttaagcgatc agcttggctt tgaaaaaatt tatcaatctt taagcgatat gggtttaaa    1380 aacctcccta agacttgtc tattgtgtta gggagctttg ctatctcacc cattgatgcg    1440
gctgaaaagt attctttatt ttctaattac ggcaccatgc tcaaacccat gctcattgaa    1500
agcatcaccg atcaacaaaa cgatgtcaaa actttcacgc ctatggaaac caaaaagatc    1560
acttccaaag aacaggcttt tttaaccctt tcagtgctga tgaatgcggt agaaaacggc    1620
acagggaatt tggctcgcat taaaggttta gaaatcgccg gtaaaacgg aacttctaac    1680 aacaacattg acgcttggtt cattggcttt acccccacct tacaaagcgt gatctggttt    1740
gggagagacg ataacacgcc tattagcaaa ggagcgacag gaggcgttgt gagtgcacct    1800
```

```
gtgtattcgt atttcatgcg taatatttta gcgattgaac cttctttaaa aagaaagttt    1860
gatgtcccca aaggcttgcg taaagaaatc gtggataaaa tcccctacta ttcaacccccc   1920 aattccatca ccccaacccc caaaagaaca gacgatagcg aagaacccctt attgttctaa   1980
```

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide reverse

<400> SEQUENCE: 5

```
tcagtgaaat tgtagtggag gtgaaaa                                         27
```

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide forward

<400> SEQUENCE: 6

```
cagtgctaag ttgtagtaaa ggtcca                                          26
```

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide reverse

<400> SEQUENCE: 7

```
tgatgtgatt ggtaaatacc a                                               21
```

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide forward

<400> SEQUENCE: 8

```
ttctatgcgc ttggaattag t                                               21
```

<210> SEQ ID NO 9
<211> LENGTH: 18
<212> TYPE: DNA
<213> ORGANISM: Artificial Sequence
<220> FEATURE:
<223> OTHER INFORMATION: Oligonucleotide reverse

<400> SEQUENCE: 9

```
tggcgataac gccgcagc                                                   18
```

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide forward

<400> SEQUENCE: 10

```
gaattagtgg atgggcag                                                   18
```

```
<210> SEQ ID NO 11
<211> LENGTH: 19
<212> TYPE: DNA
<213> ORGANISM: Artificial Sequence
<220> FEATURE:
<223> OTHER INFORMATION: Oligonucleotide reverse

<400> SEQUENCE: 11
ggcaattata gtaaaaaca                                                    19

<210> SEQ ID NO 12
<211> LENGTH: 19
<212> TYPE: DNA
<213> ORGANISM: Artificial Sequence
<220> FEATURE:
<223> OTHER INFORMATION: Oligonucleotide forward

<400> SEQUENCE: 12
gggcttgtaa ccttgcaga                                                    19

<210> SEQ ID NO 13
<211> LENGTH: 14
<212> TYPE: DNA
<213> ORGANISM: Artificial Sequence
<220> FEATURE:
<223> OTHER INFORMATION: Normal probe S23

<400> SEQUENCE: 13
aagacggaaa gacc                                                         14

<210> SEQ ID NO 14
<211> LENGTH: 16
<212> TYPE: DNA
<213> ORGANISM: Artificial Sequence
<220> FEATURE:
<223> OTHER INFORMATION: S23 mutated probe

<400> SEQUENCE: 14
caagacggag agacct                                                       16

<210> SEQ ID NO 15
<211> LENGTH: 16
<212> TYPE: DNA
<213> ORGANISM: Artificial Sequence
<220> FEATURE:
<223> OTHER INFORMATION: GyrA normal probe

<400> SEQUENCE: 15
tagtgagaat ggcgca                                                       16

<210> SEQ ID NO 16
<211> LENGTH: 16
<212> TYPE: DNA
<213> ORGANISM: Artificial Sequence
<220> FEATURE:
<223> OTHER INFORMATION: Mutant gyrA Asn87Lys probe

<400> SEQUENCE: 16
tagtgagaaa ggcgca                                                       16

<210> SEQ ID NO 17
<211> LENGTH: 16
<212> TYPE: DNA
<213> ORGANISM: Artificial Sequence
<220> FEATURE:
<223> OTHER INFORMATION: Mutant gyrA Asn87Lys probe
```

```
<400> SEQUENCE: 17
tagtgagaag ggcgca                                                    16

<210> SEQ ID NO 18
<211> LENGTH: 13
<212> TYPE: DNA
<213> ORGANISM: Artificial Sequence
<220> FEATURE:
<223> OTHER INFORMATION: GyrA normal probe

<400> SEQUENCE: 18
gcaagatttt tct                                                       13

<210> SEQ ID NO 19
<211> LENGTH: 13
<212> TYPE: DNA
<213> ORGANISM: Artificial Sequence
<220> FEATURE:
<223> OTHER INFORMATION: GyrA mutated probe Asp91Gly

<400> SEQUENCE: 19
gcaaggtttt tct                                                       13

<210> SEQ ID NO 20
<211> LENGTH: 13
<212> TYPE: DNA
<213> ORGANISM: Artificial Sequence
<220> FEATURE:
<223> OTHER INFORMATION: GyrA mutated probe Asp91Tyr

<400> SEQUENCE: 20
gcaatatttt tct                                                       13

<210> SEQ ID NO 21
<211> LENGTH: 14
<212> TYPE: DNA
<213> ORGANISM: Artificial Sequence
<220> FEATURE:
<223> OTHER INFORMATION: PBP-1 normal probe

<400> SEQUENCE: 21
tcccagcaat tatt                                                      14

<210> SEQ ID NO 22
<211> LENGTH: 14
<212> TYPE: DNA
<213> ORGANISM: Artificial Sequence
<220> FEATURE:
<223> OTHER INFORMATION: Mutable probe PBP-1 Ser413Arg

<400> SEQUENCE: 22
tcccagaaat tatt                                                      14

<210> SEQ ID NO 23
<211> LENGTH: 14
<212> TYPE: DNA
<213> ORGANISM: Artificial Sequence
<220> FEATURE:
<223> OTHER INFORMATION: Mutable probe PBP-1 Ser413Arg

<400> SEQUENCE: 23
tcccaggaat tatt                                                      14

<210> SEQ ID NO 24
```

```
<211> LENGTH: 212
<212> TYPE: DNA
<213> ORGANISM: Helicobacter pylori
<220> FEATURE:
<221> NAME/KEY: misc_feature
<222> LOCATION: (109)..(109)
<223> OTHER INFORMATION: n is a or g

<400> SEQUENCE: 24
ttaaataccg acctgcatga atggcgaacg agatgggagc tgtctcaacc agagattcag      60
tgaaattgta gtggaggtga aaattcctcc tacccgcggc aagacggana gaccccgtgg     120
acctttacta caacttagca ctgctaatgg gaatatcatg cgcaggatag gtgggaggct     180
ttgaagtaag ggctttggct cttatggagc ca                                   212
```

METHOD FOR DETERMINING HELICOBACTER PYLORI

TECHNICAL FIELD

The present invention relates to an in vitro method for determining *Helicobacter pylori* in a biological sample isolated from an individual. Furthermore, the method of the present invention also enables the determination of the antibiotic resistance of *Helicobacter pylori*.

A further aspect of the present invention relates to a kit for implementing said method.

REFERENCE TO SEQUENCE LISTING

The present application is being filed along with a Sequence Listing in electronic format. The Sequence Listing is provided as a file entitled 29715138_1, created Jan. 9, 2019, which is 11.7 Kb in size. The information in the electronic format of the Sequence Listing is incorporated herein by reference in its entirety.

STATE OF THE ART

*Helicobacter pylori* (Hp) is a microaerophilic, acidophilic flagellated Gram-negative bacterium belonging to the genus Helicobacter.

At present, Hp is a bacterium that colonises the stomach of about half of the world population and is considered an etiopathogenetic factor in peptic ulcers and MALT lymphoma, a risk factor for gastric adenocarcinoma and a factor associated with other gastric and extragastric pathologies.

It is well known that Hp infection is correlated to a low socioeconomic status rather than the race one belongs to. In fact, Hp infection is very widespread in developing countries. The modes of transmission of this bacterium are still unknown; however, the oral or faecal-oral route is deemed most likely.

The methods for the diagnosis of Hp infection are classifiable as: 1) invasive methods, in particular endoscopy with a biopsy taken of the gastric mucosa and subsequent analysis; and 2) non-invasive methods, for example the breath test, testing for the antigen in faeces or testing for antibodies in the blood.

One of the most common non-invasive methods is the urea breath test (UBT). The method entails having the patient drink a beverage containing urea marked with a radioactive carbon isotope. In the presence of Hp, the urea catalysed by urease splits, resulting in the formation and release of ammonium and marked carbon dioxide in the exhaled air. If the breath analysis of the individual reveals the presence of marked $CO_2$, the test is positive and the individual is thus considered to be infected by Hp.

Serological tests entail looking for IgG antibodies targeting Hp. However, these tests do not enable an active infection to be distinguished from a previous Hp infection. Therefore, they are not considered ideal for monitoring the effectiveness of a therapy or even as a post-test to confirm eradication.

A further minimally invasive method is based on testing for the antigen in faeces (HpSA). In this case the immunoenzymatic test is conducted on a faeces sample of an individual.

This method is a valid alternative to the breath test, but it is characterised by low sensitivity and specificity, particularly when it is desired to evaluate the effect of therapy.

With regard to therapies for eradicating Hp infection, the most common ones include the administration of proton pump inhibitors (PPI) associated with antibiotics.

In particular, the first-line therapy (Line I) actually consists in a triple therapy, which provides for the administration of PPIs and clarithromycin for 14 days, then the administration of PPIs, clarithromycin and amoxicillin or levofloxacin and metronidazole for 7-10 days. Alternatively, a sequential therapy is available; it provides for the administration of 1 gram x2 of amoxicillin and a PPI for 5 days, and then, for the next 5 days, 500 mg of clarithromycin x2, PPI and 500 mg x2 of tinidazole.

Unfortunately, resistance to antibiotics is the most important factor for the lack of success of this therapeutic approach. In particular, the widespread use of clarithromycin for the treatment of respiratory illnesses and gynaecological and parasitic infections has increased the primary resistance to this antibiotic.

Clarithromycin, like all macrolides, performs its antibacterial action by bonding to the 50S subunit of the bacterial ribosome. This bond prevents the translocation of the peptide from the A-site to the P-site of the ribosome (by blocking the enzyme translocase) and causes inhibition of the elongation of the peptide chain (by blocking the enzyme transferase).

Resistance to levofloxacin and amoxicillin are also fairly widespread.

The use of levofloxacin for the eradication of Hp is a common practice because of its role in "second-line therapy" regimes after the failure of clarithromycin-based treatments. Fluoroquinolones exert a dose-dependent bacterial effect by bonding to the A subunit of DNA gyrase (topoisomerase II), an enzyme that is essential for maintaining the helical structure of DNA. In sensitive strains, levofloxacin blocks DNA synthesis and, at high doses, RNA synthesis as well.

Amoxicillin is an aminopenicillin with an activity similar to that of ampicillin, characterised by good stability vis-à-vis gastric acidity and a greater oral bioavailability than penicillin and ampicillin. Like penicillins, amoxicillin acts on the bacterial wall, preventing the formation of cross-links (process of transpeptidation) necessary to assure the rigidity of the wall itself. It forms a stable, inactive complex with transpeptidase, the enzyme responsible for the process of transpeptidation. Amoxicillin possesses a spectrum of action that includes both Gram-positive and Gram-negative bacteria and there are basically three mechanisms of resistance:

1) Production of beta lactamase enzymes which inactivate the antibiotic by opening the beta-lactam ring;
2) Reduction of the bacteria's permeability to the molecule; and
3) Modification of the proteins that bind amoxicillin, or penicillin binding proteins (PBPs).

Amoxicillin was the first antibiotic to be used to eradicate Hp and is still today used in common therapeutic schemes, due also to its low resistance rate.

In light of the foregoing, there continues to be a highly felt need to have techniques capable of determining *Helicobacter pylori*, that is, techniques that make it possible to diagnose an infection by this bacterium in an individual and which are non-invasive, economical, fast and diagnostically accurate. In particular, there is a strongly felt need to have methods capable of determining the presence of *Helicobacter pylori* in a sample and of simultaneously evaluating the antibiotic resistance of the bacterium. The Applicant has found a solution for the above-described needs with a method, which is carried out in vitro on a biological sample isolated from an individual and provides for a molecular analysis, preferably, genotyping, of a region comprising the mutation sites of *Helicobacter pylori* gene responsible, when mutated, for resistance to the antibiotics generally used in therapies to combat infection by this bacterium, preferably clarithromycin, levofloxacin and amoxicillin.

In fact, the Applicant has unexpectedly found that the method described hereunder is very reliable compared to the presently available non-invasive methods, which are characterised by low specificity because they give many false positives.

A particular advantage of the method of the present invention is that, besides determining the presence of Hp in a biological sample, i.e. an infection by this bacterium, it simultaneously enables a determination of whether the strain of Hp identified carries a mutation responsible for resistance to one of the antibiotics used in eradication therapies. Therefore, using the method devised by the Applicant, it is possible, with a single non-invasive, fast, highly sensitive and specific test, both to determine an infection by Hp, and to determine the antibiotic resistance of the bacterium, preferably its resistance to clarithromycin, levofloxacin or amoxicillin.

Therefore, the method of the present invention proves to be highly advantageous from a therapeutic standpoint because from the earliest stages the patient can be guided toward the most suitable treatment for the purpose of eradicating the bacterium. In other words, the patient will undertake an ad hoc treatment, of greater therapeutic success, from the earliest stages.

The method of the present invention also has advantages for the health service, as it will see the elimination of the wastefulness associated with the presently available therapeutic approaches designed to eradicate the bacterium, which are based on actual eradication attempts with the various available pharmacological therapies.

Therefore, the subject matter of the present invention relates to a method for determining/monitoring *Helicobacter pylori*, and/or, in particular, for determining the resistance of *Helicobacter pylori* to the antibiotics generally used for therapeutic purposes, as specified in the appended independent claims.

Moreover, the subject matter of the present invention further relates to a kit for implementing the method as specified in the appended independent claims.

The preferred aspects of the method and kit of the present invention are defined in the appended dependent claims.

Additional features and advantages of the present invention will become more apparent from the detailed description and illustrative, non-limiting examples that follow, which also refer to the appended figure.

BRIEF DESCRIPTION OF THE DRAWING

FIG. 1 shows a diagram of the implementation of the amplification step of the method of the present invention.

DETAILED DESCRIPTION

The present invention relates to a method, carried out in vitro on a biological sample isolated from an individual, for determining, or also for monitoring, the presence of *Helicobacter pylori* (Hp) within said sample and/or for determining the resistance of Hp to at least one antibiotic, said method comprising the following steps:
(i) Obtaining a biological sample isolated from an individual;
(ii) Purifying (isolating) the DNA from said sample; and
(iii) Amplifying at least one portion of an Hp gene comprising at least one nucleotide site which, when mutated, is responsible for the resistance to said antibiotic, said amplification being performed by PCR, preferably real-time PCR, using at least one pair of oligonucleotides (pair of primers) and at least two oligonucleotide probes, where the pair of primers is paired in the region of nucleic acid straddling said mutation site, said oligonucleotide probes being marked with two different markers, and wherein at least one oligonucleotide probe is complementary and specific to at least one portion of an Hp gene comprising the at least one normal site (i.e. complementary to the normal/non-mutated allele of said gene) and at least one oligonucleotide probe is complementary and specific to at least one portion of an Hp gene comprising the at least one mutated site responsible for said antibiotic resistance (i.e. complementary to the mutated allele of said gene) (see FIG. 1);
(iv) Quantifying the amplified normal and/or mutated DNA by measuring the levels of the two markers where:
the absence of amplified DNA means the absence of Hp in the sample;
the presence of only the marker with which the probe complementary to and specific for the wild-type allele of said gene is marked defines a normal homozygous genotype and hence the presence of said Hp which is not resistant to said antibiotic;
the presence of only the marker with which the probe complementary to and specific for the mutated allele of said gene is marked defines a mutated homozygous genotype and hence the presence of said Hp which is resistant to said antibiotic; and
the presence of both markers defines a heterozygous genotype with a wild-type allele and a mutated allele of said gene, and thus the presence of said Hp which is resistant to said antibiotic.

FIG. 1 schematises step (iii); practically, the pair of forward and reverse primers are straddling (each on a strand of DNA) the site responsible, when mutated, for the antibiotic resistance. This pair enables the amplification of the region of the Hp gene containing the mutation site that is the cause of the antibiotic resistance. The pair of probes is selected in such a way that one specifically hybridizes with the region of the normal (wild-type), i.e. non-mutated gene, and the other hybridizes with the region of the gene containing the mutation. The two are marked with two different markers so that the detection of one marker or both may enable the determination of the Hp genotype. Clearly, if the bacterium is absent from the sample, there will be no amplification, because the primers will not find DNA to pair with. Detection taking place according to step (iv) makes it possible to determine the genotype of any Hp present within said sample, said genotype being normal homozygous if the amplified gene portion does not have the mutation, or mutated homozygous if the amplified gene portion has the mutation, or heterozygous if the amplified gene portion is half non-mutated and half mutated.

Thus the presence of amplified product signifies the presence of Hp in said biological sample, thus of infection by Hp, whilst the genotyping as described above makes it possible to determine whether the bacterium is resistant or not to at least one antibiotic.

The antibiotics to which the present invention makes reference are the ones generally used, individually or in combination, for the purpose of therapeutically treating Hp infection. Preferably, the antibiotic is selected in the group consisting in: clarithromycin, levofloxacin, amoxicillin, metronidazole, tinidazole, tetracycline, rifabutin and combinations thereof. For the purposes of the present invention, the preferred antibiotics are selected from among: clarithromycin, levofloxacin, amoxicillin and combinations thereof, most preferably clarithromycin.

In the context of the present invention, resistance to antibiotics means the mechanism whereby a bacterium, in this case Hp, becomes resistant to the antibiotic or pool of antibiotics used in the eradication therapy. The antibiotics to which reference is being made are the ones mentioned above.

Therefore, the method of the present invention makes it possible to determine/monitor Hp infection in an individual and simultaneously to determine the antibiotic resistance of any determined/monitored Hp strain. Consequently, the method of the present invention also enables the determination of pathologies associated with Hp infection, above all pathologies affecting the gastric system, preferably gastritis, peptic ulcer, gastric cancer, or MALT lymphoma, dyspepsia, sideropenic anaemia, idiopathic thrombocytopenic purpura, and extragastroduodenal pathologies.

In a preferred embodiment of the invention, the method is carried out on a faeces sample isolated from an individual.

The faecal sample can be collected by the individual him/herself, i.e. step (i) of the method can be carried out by the individual autonomously.

In general, the faecal sample is collected using any device suitable for the collection of faeces. Preferably, the device comprises a portion for collecting faeces and solubilising them in a solubilisation chamber containing a solubilisation means. The solubilisation means is preferably a saline solution like PBS. Solubilisation enables homogenization of the faeces sample and is preferably carried out/favoured by vigorously shaking the sample, for example on a Vortex mixer for several seconds (about 30 seconds).

The faeces are preferably collected with a brush suitable for collecting an appropriate amount of faeces for implementing the method of the present invention. In particular, the amount to be collected in order to implement the method of the invention (thus the amount of the starting material of the method) ranges from 150 to 250 milligrams (mg); preferably, it is about 200 mg of faeces.

For the purpose of implementing the method of the present invention, it is advisable to solubilise from 150 to 250 mg, preferably about 200 mg of faeces, in about 1 ml of a solubilisation means.

The solubilisation chamber is separated, preferably by means of a filtering element, from a collection chamber. In this way, the solubilised faeces can pass, for example, by gravity through the filter in the collection chamber. The portion of solubilised faeces of larger dimensions than the pores of the filter will not pass into the collection chamber. The filtered faeces can be collected from the collection chamber, preferably though a membrane that is penetrable, for example, with a syringe.

For the purposes of the present invention, the pore size of the filtering element preferably ranges from 100 to 200 microns ($\mu m$), more preferably from 100 to 150 $\mu m$, even more preferably from 105 to 120 $\mu m$, and even more preferably it is about 106 $\mu m$. Thus the solubilised/filtered portion of faeces that will pass will have dimensions equal to/less than 100-200 $\mu m$, preferably equal to/less than 100-150 $\mu m$, more preferably equal to/less than 105-120 $\mu m$, more preferably equal to/less than about 106 $\mu m$.

Once a biological sample has been obtained from an individual or once the faeces have been solubilised and/or filtered as described above, the biological sample or the solubilised/filtered faeces (hereinafter sample) will be subjected to step (ii) of the method.

DNA is extracted from the sample using the methods generally known to every person skilled in the art for the specific purpose. For the purposes of the present invention, the preferred extraction method comprises the use of a phenol-chloroform solution, preferably in 1:1 ratio with the sample to be treated.

In particular, the extraction method of the present invention comprises a step of adding Trizol to the sample. Preferably, the ratio between Trizol and the sample is 1:1. The Trizol:sample mixture is then preferably evenly mixed for a few seconds, for example on a Vortex mixer.

Chloroform is preferably subsequently added to the Trizol:sample mixture. It is preferable to add an amount of chloroform equal to 1/10 of the volume of the Trizol:sample mixture.

Preferably, the Trizol:sample:chloroform mixture is evenly mixed for a few seconds, for example on a Vortex mixer.

Preferably, after being evenly mixed, the Trizol:sample:chloroform mixture is stratified, preferably by centrifugation. It is advisable to centrifuge at 10000-14000 g, preferably about 12000 g, for a time that is preferably about 10 minutes. The stratification is carried out, preferably, at a low temperature, more preferably at about 4° C.

At the end of the stratification of the Trizol:sample:chloroform mixture, 3 phases are usually obtained: an aqueous phase, an interphase and a phenol phase.

For the purposes of the present invention it is preferable to discard the aqueous phase.

Therefore, the DNA is precipitated from the remaining part of the mixture, i.e. from the interphase and phenol phase, which represent the organic phase.

Precipitation is preferably achieved by adding an alcohol such as ethanol, more preferably 100% ethanol, to the organic phase.

Then the precipitated DNA is preferably made to sediment, for example, by centrifugation. The preferred centrifugation conditions are about 2000 g for a few minutes, preferably at a cold temperature, for example about 4° C.

Once the DNA has precipitated (practically, the DNA forms a pellet), it is preferable to remove the surface phase and the precipitated DNA is treated, preferably, at least once, more preferably, 2-3 times, with a saline solution such as sodium citrate (this step is a sort of washing of the DNA pellet). This step is preferably carried out at room temperature, more preferably for about 30 minutes.

Every treatment with saline solution is followed by a step of sedimentation of the precipitated DNA, preferably by centrifugation, for example at about 2000 g for a few minutes, preferably at a low temperature (for example about 4° C.).

Subsequently, the precipitated DNA is preferably treated with an alcohol such as ethanol, preferably 75% ethanol. Said treatment is preferably carried out for about 20-30 minutes, more preferably at room temperature.

At the end of the treatment with alcohol, the precipitated DNA is preferably made to sediment, for example by centrifugation at about 2000 g for a few minutes, preferably at a low temperature (for example about 4° C.).

Then the precipitated DNA is preferably dried so as to permit the alcohol to evaporate completely.

The dried DNA is preferably re-suspended in an alkaline solution, more preferably in NaOH (for example NaOH 8 mM).

At the end of step (I), it is preferable to carry out a final centrifugation step at the maximum speed (about 14000 g) for ten minutes or so, preferably at room temperature. The supernatant (i.e. the part that has not precipitated) is transferred and a buffer is added to it, for example HEPES-EDTA, preferably at pH 7-8.

Before using the DNA for the subsequent step (iii), it is advisable to evaluate the above-described purified DNA quantitatively and/or qualitatively, for example by means of the techniques known to every person skilled in the art (260/280 nm spectrophotometer reading, visualization of a DNA sample on agarose gel, etc . . . ).

The step of amplifying at least one portion of an Hp gene comprising at least one nucleotide site which, when mutated, is responsible for the resistance to said antibiotic takes place by PCR, preferably real-time PCR, more preferably real-time PCR with TaqMan chemistry.

In the real-time PCR system, monitoring the accumulation of the amplification (amplified) product is made possible thanks to the marking of the oligonucleotide probes.

Each oligonucleotide probe used in step (iii) of the method is marked with at least two different markers, preferably fluorescent. In particular, a high-intensity fluorescent marker, defined as the reporter, for example a modified fluorescein, and a second marker, preferably a low-intensity or non-fluorescent marker, referred to as the quencher, for example a modified rhodamine.

Preferably, the reporter is bonded to the 5' end of the probe and/or preferably the quencher is bonded to the 3' end of the probe.

Thanks to the non-fluorescence of the quencher, the real-time PCR systems are able to measure the inputs of the reporter fluorochromes with greater accuracy. When the reporter and quencher are close (near) to each other, the probe itself—the quencher—absorbs the fluorescence of the reporter which, therefore, cannot be measured. In fact, the only detectable fluorescence under these conditions is the low fluorescence of the quencher.

During PCR, each probe performs a specific annealing (pairing) with its complementary sequence in the region straddling the pair of primers (the forward primer and the reverse primer—see FIG. 1).

The DNA polymerase not only duplicates the target DNA, but, with its 5'-3' endonuclease activity, it also degrades the oligonucleotide probe hybridized to it by separating the two fluorescent markers and thus rendering the emission of the reporter fully detectable. Given that for every DNA pair duplicated during real-time PCR, the freeing of a reporter molecule (fluorescent marker) takes place, the relative fluorescence that is accumulated during the amplification process is proportional at every moment to the amount of amplified DNA. Throughout the entire duration of the real-time PCR reaction, via an emission spectrum acquisition program, for example the Sequence Detection System (SDS), it is possible to convert the variation in fluorescence of the reporter measured by the program into a real-time representation of the amplification kinetics.

The PCR cycle in which the fluorescence threshold value of the reporter is reached, due not to a mere variation in the "background noise" of the system, but rather to a specific amplification event, is defined as the threshold cycle (Ct) of the reaction. In the method of the present invention, the target DNA is quantified at the threshold cycle, thus when the PCR reaction is in an exponential phase.

Since the two oligonucleotide probes, one for the normal allele of the Hp gene and the other for the mutated allele (i.e. the one carrying the mutation responsible for the antibiotic resistance of Hp), are marked with two different reporters (the fluorescence signal emitted is different) it will be possible to trace the alleles that have been amplified and hence the genotype of the bacterium.

Thus the amplification step enables the genotyping of the bacterial strain, that is, it enables the unknown genotype of a sample to be determined. By means of the amplification of the present invention, it will preferably be possible to differentiate a polymorphism associated with a mutation of a single nucleotide, i.e. a point mutation or an SNP (single nucleotide polymorphism). In this case, the SNP falls within the Hp gene responsible, when mutated, for the antibiotic resistance. Alternatively, the amplification of the present invention will make it possible to differentiate a mutation of a single nucleotide which determines the translation of the triplet in which said nucleotide falls into an amino acid differing from the one present in the normal protein.

Preferably, in the context of the present invention, single nucleotide polymorphism (SNP) means a polymorphism, i.e. a (genetic) variation in gene material (DNA), which affects a single nucleotide, and is such that the polymorphic allele is present in the population in a proportion greater than 1%. Below this threshold one usually speaks of a rare variant.

Preferably, the genetic variation can be caused by substitutions, deletions or insertions of bases in the DNA and can regard coding and non-coding regions. The polymorphic loci are those for which at least 2% of the population is heterozygous. The consequences of these polymorphisms can be silent when the protein variation does not alter the function or structure of the protein. Alternatively, said polymorphisms can have non-silent consequences, in particular, when one observes a change in phenotype, for example when the proteins are functionally altered.

The genotyping step is carried out by amplifying at least one portion of the sequence of the Hp gene comprising the site which, if mutated, is responsible for antibiotic resistance with at least one pair of oligonucleotides (pair of primers) that are complementary to a region of said portion. Practically, the at least one mutation site causing antibiotic resistance falls between the pair of primers, i.e. the region amplified with the pair of primers comprises the portion of the sequence of the Hp gene containing at least one mutation site responsible for antibiotic resistance.

Said gene is preferably selected from among: 23S rRNA, gyrA and PBP-1.

The 23S rRNA gene is responsible, if mutated, for resistance to clarithromycin. In particular, in this case, with the method of the present invention, it is possible to determine at least one of the most widespread mutations falling in the 23S rRNA gene which are responsible for most of the clarithromycin resistance. Preferably, said mutations responsible for clarithromycin resistance are selected from among: the A2143G mutation (i.e. the adenine in position 2143 is modified into guanine), the A2142C mutation and the A2142G mutation.

The gyrA gene is responsible, if mutated, for resistance to levofloxacin. In particular, in this case, with the method of the present invention, it is possible to determine at least one of the mutations affecting the amino acid asparagine at position 87 which, due to the mutation, becomes a lysine. Specifically, at position 87 there can be two normal (wild-type) variants, or the AAC triplet or AAT triplet which encode for the amino acid asparagine. The mutations that affect the third base of these triplets and transform them into AAA or AAG lead to the substitution of asparagine with lysine.

Therefore, preferably, said mutations responsible for levofloxacin resistance are selected between: the C261A and C261G mutations.

Furthermore, with the method of the present invention, it is possible to determine the mutations that affect aspartic acid at position 91, which, due to the mutation, becomes a glycine, or an asparagine, or an alanine, or a tyrosine.

Specifically, the triplet at position 91, i.e. the GAT sequence (which encodes for aspartic acid), is substituted, at the site of the first nucleotide base, with the GGT triplet (which encodes for glycine) or the TAT triplet (which encodes for tyrosine).

Therefore, the mutations responsible for levofloxacin resistance determined with the method of the present invention are preferably selected from among: G271A, G271T and A272G.

The PBP-1 gene is responsible, if mutated, for resistance to amoxicilin. In particular, the mutation causes the amino acid substitution of a serine with an arginine at position 413 (Ser-413Arg). The AGC triplet which encodes a serine can be mutated, in the third base, into the triplet AGA or AGG, which encode an arginine.

Preferably the mutations responsible for amoxicillin resistance determined with the method of the present invention are selected from among: C413A and C413G.

In particular, said amplified portion of the Hp gene sequence is selected from among SEQ ID NO: 1-4, where SEQ ID NO: 1 and/or 2 refer to the 23S gene, SEQ ID NO:3 refers to the gyrA gene and SEQ ID NO: 4 refers to the PBP-1 gene.

Preferably, the pair of primers comprises SEQ ID NO: 5 and SEQ ID NO: 6. Said pair of primers enables amplification of the sequence SEQ ID NO: 1 and/or 2, i.e. the portion of the sequence of the 23S rRNA gene of Hp comprising at least one of the mutation sites responsible for the clarithromycin resistance of Hp.

Alternatively, the pair of primers comprises SEQ ID NO: 9 and SEQ ID NO: 10. Said pair of primers enables amplification of the sequence SEQ ID NO: 3, i.e. the portion of the sequence of the gyrA gene of Hp comprising at least one of the mutation sites responsible for the lexofloxacin resistance of Hp.

Alternatively, the pair of primers comprises SEQ ID NO: 13 and SEQ ID O: 14. Said pair of primers enables amplification of the sequence SEQ ID NO: 4, i.e. the portion of the sequence of the PBP-1 gene of Hp comprising at least one of the mutation sites responsible for the amoxicillin resistance of Hp.

Optionally, more than one pair of primers can be used in a single amplification reaction in order to simultaneously determine/monitor more than one antibiotic resistance of Hp, in particular, to determine/monitor the clarithromycin resistance and/or lexofloxacin resistance and/or amoxicillin resistance of an Hp strain.

The amplification is carried out using at least two oligonucleotide probes in addition to the pair of primers. Each oligonucleotide probe is marked with a high-intensity marker (reporter) at one end, preferably the 5' end, and a non-fluorescent or low-intensity marker (quencher) at the other end, preferably 3'. Furthermore, of the two oligonucleotide probes, one is complementary and specific to the normal allele of said gene and one is complementary and specific to the mutated allele responsible for said antibiotic resistance (see FIG. 1).

The oligonucleotide probes are preferably marked with a marker selected from among: FAM (with red fluorescence), VIC (with green fluorescence), HEX, JOE, NED, SYBER, TAMRA, TET and ROX.

As amply explained earlier, when these two fluorescent markers are present on the same oligonucleotide probe, the quencher sequesters (absorbs) the fluorescence emitted by the reporter, whereas when they are separated, for example as occurs as a result of degradation by the DNA polymerase, the fluorescence of the reporter is not absorbed by the quencher and can thus be detected/measured.

Therefore, in the context of the present invention, quencher means a low-energy fluorescent marker (fluorophore, for example a modified rhodamine), which extinguishes the fluorescence of the reporter and thus, when the probe is intact, only its own fluorescence is measurable. Preferably, the probe is a TaqMan probe with minor groove binder (MGB) chemistry. Probe with minor groove binder chemistry means a system in which the probe is marked with at least two different fluorescent substances, for example VIC and FAM. This chemistry makes it possible to increase the melting temperature ™ of a probe without increasing its length and therefore enables short probes to be designed.

Preferably, the probe is selected from among SEQ ID NO: 13-23.

In particular, SEQ ID NO: 13 and/or SEQ ID NO: 14 are used with the pair of primers SEQ ID NO: 5 and SEQ ID NO: 6, SEQ ID NO: 13 being complementary to at least one portion of the 23S rRNA gene, preferably SEQ ID NO: 1 and/or 2, without the mutation responsible for antibiotic resistance; and SEQ ID NO: 14 being complementary to at least one portion of the 23S rRNA gene, preferably SEQ ID NO: 1 and/or 2 carrying a mutation responsible for antibiotic resistance, preferably selected from among: the A2143G mutation, A2142C mutation and A2142G mutation. Or SEQ ID NO: 3 is specific for the normal allele and SEQ ID NO: 4 for the one carrying the mutation responsible for clarithromycin resistance.

Preferably, at least one probe selected from among: SEQ ID NO: 15, 16, 17 and combinations thereof is used with the pair of primers SEQ ID NO: 7 and 8. In particular, SEQ ID NO: 15-17 are complementary and specific to a portion of the sequence SEQ ID NO: 3 containing at least one of the mutation sites responsible for levofloxacin resistance. SEQ ID NO: 15 is specific to the normal allele of the gyrA gene and SEQ ID NO: 16 and 17 are specific to the Asn87Lys mutations.

Preferably, at least one probe selected from among: SEQ ID NO: 18, 19, 20 and combinations thereof, is used with the pair of primers SEQ ID NO: 9 and 10. In particular, SEQ ID NO: 18-20 are complementary and specific to a portion of the sequence SEQ ID NO: 3 containing at least one of the mutation sites responsible for levofloxacin resistance. SEQ ID NO: 18 is specific for the normal allele of the gyrA gene and SEQ ID NO: 19 and 20 are specific, respectively, for the Asp91Gly mutation and Asp91Tyr mutation.

Preferably, at least one probe selected from among: SEQ ID NO: 21, 22, 23 and combinations thereof is used with the pair of primers SEQ ID NO: 11 and 12. In particular, SEQ ID NO: 21-23 are complementary and specific to a portion of the sequence SEQ ID NO: 4 containing at least one of the mutation sites responsible for amoxicillin resistance. SEQ ID NO: 21 is specific for the normal allele of the PBP-1 gene and SEQ ID NO: 22 and 23 are specific for the Ser413Arg mutation.

The sequences used in the method of the present invention are shown in Table I. In particular, the table shows the SEQ ID NO of the sequence, the name of the sequence which takes into account its function in the method of the invention and the sequence itself.

The sequences of the present invention are provided in the appended Sequence Listing. The sequences contained in the appended Sequence Listing are to be understood as incorporated in the present description.

The subject matter of the present invention should also be considered to include the sequences characterised by at least 70%, 80%, 85%, 90%, or 95% identity to SEQ ID NO: 1-23 listed in Table I and described in their entirety in the appended Sequence Listing.

TABLE I

| | | |
|---|---|---|
| SEQ ID NO: 1 | ACAGCGATGTGGTCTCAGCAAAGAGTCCCTCCCGACTGTTTA<br>CCAAAAACACAGCACTTTGCCAACTCGTAAGAGGAAGTATAA<br>GGTGTGACGCCTGCCCGGTGCTCGAAGGTTAAGAGGATGCG<br>TCAGTCGCAAGATGAAGCGTTGAATTGAAGCCCGAGTAAACG<br>GCGGCCGTAACTATAACGGTCCTAAGGTAGCGAAATTCCTTG<br>TCGGTTAAATACCGACCTGCATGAATGGCGAACGAGATGGGA<br>GCTGTCTCAACCAGAGATTCAGTGAAATTGTAGTGGAGGTGA<br>AAATTCCTCCTACCCGCGGCAAGACGGA[A/G]AGACCCCGTG<br>GACCTTTACTACAACTTAGCACTGCTAATGGGAATATCATGCG<br>CAGGATAGGTGGGAGGCTTTGAAGTAAGGGCTTTGGCTCTTA<br>TGGAGCCATCCTTGAGATACCACCCTTGCATGTTTCTGTTAGC<br>TAACTGGCCTGTGTTATCCCAGGCAGGACAATGCTTGGTGGG<br>TAGTTTGACTGGGGCGGTCGCCTCCTAAAAAGTAACGGAGGC<br>TTGCAAAGGTTGGCTCATTGCGGTTGGAAATCGCAAGTTGAG<br>TGTAATGGCACAAGCCAGCCTGACTGTAAGACATACAAGTCA<br>AGCAGAGACGAA | Portion of the 23S<br>rRNA gene |
| SEQ ID NO: 2 | TTAAATACCGACCTGCATGAATGGCGAACGAGATGGGAGCTG<br>TCTCAACCAGAGATTCAGTGAAATTGTAGTGGAGGTGAAAATT<br>CCTCCTACCCGCGGCAAGACGGAAAGACCCCGTGGACCTTT<br>ACTACAACTTAGCACTGCTAATGGGAATATCATGCGCAGGATA<br>GGTGGGAGGCTTTGAAGTAAGGGCTTTGGCTCTTATGGAGCC<br>A | Normal amplified<br>portion of the 23S<br>rRNA gene |
| SEQ ID NO: 3 | ATGCAAGATCATTTAGTCAATGAAACAAAAAATATTGTAGAAG<br>TGGGGATTGATTCTTCTATTGAAGAGAGCTATTTGGCTTATTC<br>CATGAGCGTGATCATAGGGCGCGCTTTACCGGACGCTAGAG<br>ACGGCTTAAAGCCTGTGCATAGGCGTATTTTGTATGCGATGC<br>ATGAATTAGGCCTTACTTCCAAAGTCGCTTATAAAAAAAGCGC<br>TAGGATCGTGGGTGATGTGATTGGTAAATACCACCCCCATGG<br>CGACACCGCAGTTTATGATGCGTTAGTGAGAATGGCGCAAGA<br>TTTTTCTATGCGCTTGGAATTAGTGGATGGGCAGGGCAACTTT<br>GGCTCTATTGATGGCGATAACGCCGCAGCGATGCGTTACACT<br>GAAGCCAGAATGACCAAGGCGAGTGAAGAGATTTTAAGAGAT<br>ATTGATAAAGACACCATTGATTTTGTGCCTAATTACGATGACA<br>CCTTAAAAGAGCCAGATATTTTACCAAGCCGTCTGCCTAACCT<br>TTTAGTCAATGGGGCTAATGGGATCGCCGTAGGGATGGCGAC<br>TTCTATCCCCCCTCATAGGATTGATGAAATCATAGACGCTTTA<br>GCGCATGTCTTAGGAAACCCTAACGCTGAATTAGATAAAATTT<br>TGGAATTTGTCAAAGGACCTGACTTTCCTACTGGTGGGATCAT<br>CTATGGCAAGGCGGGTATTGTTGAAGCCTATAAAACGGGGCG<br>AGGGCGCGTGAAAGTGCGGGCCAAAGTGCATGTGGAAAAGA<br>CAAAAAATAAAGAAATCATCGTTTTAGGTGAAATGCCTTTTCAA<br>ACCAATAAAGCCAAATTAGTGGAACAAATCAGCGATTTAGCGC<br>GAGAAAAACAAATTGAAGGCATTAGCGAAGTGCGCGATGAAA<br>GCGATAGAGAGGGCATTAGAGTGGTGATTGAATTAAAAAGAG<br>ACGCGATGAGTGAAATTGTCTTAAACCACCTTTACAAACTCAC<br>CACTATGGAGACCACTTTTAGCATCATTTTACTCGCTATTTACA<br>ATAAAGAGCCTAAGATTTTCACGCTTTTAGAGTTGTTGCGCCT<br>TTTCTTAAACCATAGAAAGACCATTATTATAAGACGCACGATTT<br>TTGAATTAGAAAAGGCTAAGGCCAGAGCGCATATTTTAGAGG<br>GCTATTTGATCGCCTTGGACAATATTGATGAAATCGTGCGACT<br>CATTAAAACAAGCCCAAGCCCAGAAGCGGCTAAAAACGCCTT<br>AATAGAGCGTTTTAGTTTGAGCGAGATCCAAAGCAAAGCCATT<br>TTAGAAATGCGTTTGCAACGCTTGACAGGCCTTGAAAGAGAT<br>AAGATCAAAGAAGAATACCAAAACTTATTAGAGCTTATTGATG<br>ATCTCAATGCATTTTAAAGAGCGAAGATCGCTTGAATGAAGT<br>CGTCAAAACAGAGCTTTTAGAAGTCAAAGAGCAGTTTTCTTCT<br>CCAAGGCGCACTGAAATTCAAGAATCTTATGAAAGTATTGATA<br>CAGAAGATTTGATCGCTAATGAGCCTATGGTAGTGAGCATGA<br>GCTATAAAGGCTATGTGAAAAGAGTGGATTTAAAAGCCTATGA<br>AAGGCAAAATCGTGGCGGTAAAGGCAAGCTTTCAGGCAGCAC | Normal amplified<br>portion of the gyrA<br>gene |

TABLE I-continued

| | | |
|---|---|---|
| | TTATGAAGATGATTTCATTGAAAACTTTTTTGTGGCTAACACGC<br>ATGATATTTTGCTCTTTATCACCAATAAGGGGCAATTGTATCAT<br>TTGAAAGTCTATAAAATCCCAGAAGCGAGCCGGATCGCTATG<br>GGTAAAGCTATTGTGAATTTAATCTCACTCGCTCCTAATGAAA<br>AGATCATGGCAACCCTAAGCACTAAAGATTTTAGCGATGAAC<br>GCTCTTTAGCTTTCTTCACGAAAAATGGCGTGGTGAAGCGCA<br>CCAATTTGAGCGAATTTGGCGGTAATAGGAGTTATAGCGGTA<br>TCAGAGCGATTGTTTTAGATGAAGGCGATGAATTAGTGGGCG<br>CAAAAGTTGTGGATAAAAACGCTAAGCATTTGCTCATCGCATC<br>TTATTTGGGCATGTTCATTAAATTCCCTTTAGAAGACGTGCGC<br>GAAATAGGAAGAACTACTCGTGGGGTTATGGGTATTAGACTG<br>AATGAAAATGATTTTGTTGTCGGCGCGGTTGTCATTAGCGATG<br>ATAGCAACAAGCTTTTGAGCGTGAGCGAGAACGGGCTTGGCA<br>AGCAAACTCTAGCCGAAGCGTATAGAGAGCAATCTCGTGGAG<br>GTAAGGGGGTCATTGGCATGAAGCTCACTCAAAAGACCGGTA<br>ATTTGGTGAGCGTTATCAGCGTGGATGATGAGAACCTGAATTT<br>GATGATCCTTACCGCGAGCGCGAAAATGATTAGAGTTTCCATT<br>AAAGATATTAGAGAAACCGGAAGAAATGCCAGTGGGGTAAAA<br>CTCATAAACACCGCTGATAAAGTCGTGTATGTCAATTCTTGCC<br>CTAAAGAAGAAGAGCCAGAAAATTTAGAAACCTCTTCGGTGC<br>AAAATTTGTTTGAGTGA | |
| SEQ ID NO: 4 | ATGCTAAAAAAGATTTTTTATGGTTTTATCGTTTTATTTTTGATT<br>GTCATAGGGTTGTTAGCCATTCTTATCGCTCAAGTTTGGGTAA<br>CTACGGATAAGGATATTGCTAAAATTAAAGATTATCGCCCGGG<br>AGTCGCTTCACAGATTTTAGACCGAAAAGGGCGTTTGATCGC<br>CAATATCTATGATAAAGAATTCCGTTTTTATGCGCGTTTTGAAG<br>AAATCCCCCCACGATTTATTGAAAGCCTTTTAGCGGTAGAAGA<br>CACCCTCTTTTTTGAGCATGGGGGATCAATTTAGACGCTATC<br>ATGCGCGCTATGATTAAAAACGCTAAAAGCGGTCGCTACACT<br>GAAGGGGGTAGCACCCTAACCCAACAACTCGTTAAAAACATG<br>GTGCTCACGCGAGAAAAAACCCTAACCAGAAAACTCAAAGAA<br>GCTATCATTTCCATACGCATTGAAAAAGTCTTAAGCAAAGAAG<br>AAATTTTAGAGCGTTATTTGAACCAAACTTTTTTTGGGCATGG<br>GTATTATGGCGTGAAAACCGCAAGCTTAGGGTATTTTAAAAAA<br>CCCCTTGACAAACTCACGCTTAAAGAAATCACCATGTTAGTCG<br>CCTTGCCTAGGGCTCCGAGTTTTTATGATCCTACCAAAAATTT<br>AGAATTTTCACTCTCTAGGGCTAATGATATTTTAAGGCGGTTG<br>TATTCTTTAGGCTGGATTTCTTCTAACGAGCTCAAAGGCGCTC<br>TCAATGAAGTGCCAATCGTCTATAACCAAACTTCCACGCAAAA<br>TATCGCTCCCTATGTCGTGGATGAAGTGTTGAAGCAATTGGAT<br>CAATTAGATGGGTTAAAAACCCAAGGCTATACCATAAAGCTCA<br>CGATAGATTTGGATTACCAACGCTTAGCGTTAGAGTCCTTGC<br>GTTTTGGGTATCAAAAAATCTTAGAAAAAATCGCTAAAGAAAA<br>GCCAAAAACTAACGCATCTAACGAAAATGAAGACAATTTGAAC<br>GCTAGCATGATCGTTACAGACACGAGCACCGGTAAGATTTTA<br>GCTTTAGTGGGGGGATTGATTATAAAAAAAGCGCTTTCAATC<br>GCGCCACGCAAGCCAAACGGCAGTTTGGGAGCGCGATAAAG<br>CCTTTTGTGTATCAAATCGCTTTTGATAATGGCTATTCCACCA<br>CTTCTAAAATCCCTGATACTGCGCGAAATTTTGAAAATGGCAA<br>TTATAGTAAAAACAGCGAACAAAACCACGCATGGCATCCCAG<br>CAATTATTCTCGCAAGTTTTTAGGGCTTGTAACCTTGCAAGAA<br>GCCTTGAGCCATTCGTTAAATCTAGCCACGATCAATTTAAGCG<br>ATCAGCTTGGCTTTGAAAAAATTTATCAATCTTTAAGCGATATG<br>GGGTTTAAAAACCTCCCTAAAGACTTGTCTATTGTGTTAGGGA<br>GCTTTGCTATCTCACCCATTGATGCGGCTGAAAAGTATTCTTT<br>ATTTTCTAATTACGGCACCATGCTCAAACCCATGCTCATTGAA<br>AGCATCACCGATCAACAAAACGATGTCAAAACTTTCACGCCTA<br>TGGAAACCAAAAGATCACTTCCAAAGAACAGGCTTTTTTAAC<br>CCTTTCAGTGCTGATGAATGCGGTAGAAAACGGCACAGGGAA<br>TTTGGCTCGCATTAAAGGTTTAGAAATCGCCGGTAAAACCGG<br>AACTTCTAACAACAACATTGACGCTTGGTTCATTGGCTTTACC<br>CCCACCTTACAAAGCGTGATCTGGTTTGGGAGAGACGATAAC<br>ACGCCTATTAGCAAAGGAGCGACAGGAGGCGTTGTGAGTGC<br>ACCTGTGTATTCGTATTTCATGCGTAATATTTTAGCGATTGAAC<br>CTTCTTTAAAAAGAAAGTTTGATGTCCCCAAAGGCTTGCGTAA<br>AGAAATCGTGGATAAAATCCCCTACTATTCAACCCCCAATTCC<br>ATCACCCCAACCCCAAAAGAACAGACGATAGCGAAGAACCC<br>TTATTGTTCTAA | Normal amplified<br>portion of the pbp-1<br>gene |
| SEQ ID NO: 5 | 5' TCAGTGAAATTGTAGTGGAGGTGAAAA 3' | Reverse<br>oligonucleotide |
| SEQ ID NO: 6 | 5' CAGTGCTAAGTTGTAGTAAAGGTCCA 3' | Forward<br>oligonucleotide |
| SEQ ID NO: 7 | 5'TGATGTGATTGGTAAATACCA 3' | Reverse<br>oligonucleotide |

TABLE I-continued

| | | |
|---|---|---|
| SEQ ID NO: 8 | 5'TTCTATGCGCTTGGAATTAGT 3' | Forward oligonucleotide |
| SEQ ID NO: 9 | 5' TGGCGATAACGCCGCAGC 3' | Reverse oligonucleotide |
| SEQ ID NO: 10 | 5' GAATTAGTGGATGGGCAG 3' | Forward oligonucleotide |
| SEQ ID NO: 11 | 5' GGCAATTATAGTAAAAACA 3' | Reverse oligonucleotide |
| SEQ ID NO: 12 | 5' GGGCTTGTAACCTTGCAGA 3' | Forward oligonucleotide |
| SEQ ID NO: 13 | 5' AAGACGGAAAGACC 3' | Normal probe S23 |
| SEQ ID NO: 14 | 5' CAAGACGGAGAGACCT 3' | Probe mutata S23 |
| SEQ ID NO: 15 | 5' TAGTGAGAATGGCGCA 3' | Normal probe gyrA |
| SEQ ID NO: 16 | 5' TAGTGAGAAAGGCGCA 3' | Mutated probe gyrA Asn87Lys |
| SEQ ID NO: 17 | 5' TAGTGAGAAGGGCGCA 3' | Mutated probe gyrA Asn87Lys |
| SEQ ID NO: 18 | 5' GCAAGATTTTTCT 3' | Normal probe gyrA |
| SEQ ID NO: 19 | 5' GCAAGGTTTTTCT 3' | Mutated probe gyrA Asp91Gly |
| SEQ ID NO: 20 | 5' GCAATATTTTTCT 3' | Mutated probe gyrA Asp91Tyr |
| SEQ ID NO: 21 | 5'TCCCAGCAATTATT 3' | Normal probe PBP-1 |
| SEQ ID NO: 22 | 5'TCCCAGAAATTATT 3' | Mutated probe PBP-1 Ser413Arg |
| SEQ ID NO: 23 | 5'TCCCAGGAATTATT 3' | Mutated probe PBP-1 Ser413Arg |

According to the method of the present invention, in the same amplification reaction there will be at least two different marked probes, each with different fluorophores and each complementary to one of the alleles which, if mutated, causes antibiotic resistance. Thus an increase in fluorescence at the specific wavelength of one of the two fluorophores is compatible with a state of homozygosity for that given allele, whereas the emission of fluorescence at both wavelengths is compatible with a state of heterozygosity.

The subject matter of the present invention further relates to a kit for implementing the method according to the present invention, i.e. a kit for determining/monitoring Hp infection in an individual and simultaneously determining the antibiotic resistance of the Hp strain. Consequently, the kit also enables the determination of pathologies associated with Hp infection, above all pathologies affecting the gastric system, preferably gastritis, peptic ulcer, gastric cancer, or MALT lymphoma, dyspepsia, sideropenic anaemia, idiopathic thrombocytopenic purpura, and extragastroduodenal pathologies.

In one embodiment of the invention, the kit of the invention comprises at least one pair of oligonucleotides (pair of primers) and at least two oligonucleotide probes, where the pair of primers is paired in a DNA region of at least one Hp gene comprising at least one mutation site responsible for the resistance to an antibiotic, in particular, straddling said at least one mutation site, said oligonucleotide probes being marked with two different markers, and wherein at least one oligonucleotide probe is complementary and specific to a portion of the region of the gene of the normal allele of said gene and at least one oligonucleotide probe is complementary and specific to a portion of the region of gene of the mutated allele of said gene responsible for said antibiotic resistance.

In a preferred embodiment of the invention, the kit for determining Hp in a biological sample isolated from an individual and/or for determining the resistance of said Hp to clarithromycin provoked by a mutation of the 23S rRNA gene selected in the group consisting in: A2143G, A2142C and A2142G; and/or to levofloxacin caused by a mutation of the gyrA gene selected in the group consisting in: C261A, C261G, G271A, G271T, A272G; and/or to amoxicillin provoked by a mutation of the PBP-1 gene selected in the group consisting in C413A and C413G, comprises:
  at least one pair of primers for amplifying, by real-time PCR, at least one portion of at least one Hp gene comprising at least one mutation site responsible for the resistance to said antibiotic, said pair of primers being selected from among: SEQ ID NO: 5 and 6 for the 23S rRNA gene; SEQ ID NO: 9 and 10 for the gyrA gene; and SEQ ID NO: 13 and 14 for the pbp-1 gene; and
  at least two oligonucleotide probes marked with two different markers and wherein at least one oligonucleotide probe is complementary and specific to the at least one portion of the normal allele of at least one Hp gene comprising at least one mutation site responsible for the resistance to said antibiotic and at least one oligonucleotide probe is complementary and specific to the at least one portion of the mutated allele of at least one Hp gene comprising at least one mutation site responsible for the resistance to said antibiotic, said oligonucleotide probes being selected in the group consisting in SEQ ID NO: 13-23, where:

SEQ ID NO: 13 and/or 14 are used with the pair of primers SEQ ID NO: 5 and 6 and SEQ ID NO: 13 being complementary to at least one portion of the 23S rRNA gene, preferably SEQ ID NO: 1 and/or 2, without the mutation responsible for clarithromycin resistance; and SEQ ID NO: 14 being complementary to at least one portion of the 23S rRNA gene, preferably SEQ ID NO: 1 and/or 2, with a mutation responsible for clarithromycin resistance, selected in the group consisting in: A2143G, A2142C and A2142G;

SEQ ID NO: 15, 16 and 17 are used with the pair of primers SEQ ID NO: 7 and 8 and SEQ ID NO: 15 being complementary to at least one portion of the gyrA gene, preferably SEQ ID NO: 3, without the mutation responsible for levofloxacin resistance; SEQ ID NO: 16 and/or 17 being complementary to at least one portion of the gyrA gene, preferably SEQ ID NO: 3, with the Asn87Lys mutation responsible for levofloxacin resistance;

SEQ ID NO: 18, 19 and 20 are used with the pair of primers SEQ ID NO: 9 and 10 and SEQ ID NO: 18 being complementary to at least one portion of the gyrA gene, preferably SEQ ID NO: 3, without the mutation responsible for levofloxacin resistance; SEQ ID NO: 19 being complementary to at least one portion of the gyrA gene with the Asp91Gly mutation; and/or SEQ ID NO: 20 being complementary to at least one portion of the gyrA gene, preferably SEQ ID NO: 3, with the Asp91Ty mutation responsible for levofloxacin resistance;

SEQ ID NO: 21, 22 and 23 are used with the pair of primers SEQ ID NO: 11 and 12 and SEQ ID NO: 21 being complementary to at least one portion of the pbp-1 gene, preferably SEQ ID NO: 4, without the mutation responsible for amoxicillin resistance; and SEQ ID NO: 22 and/or 23 being complementary to at least one portion of the pbp-1 gene with the Ser413Arg mutation responsible for amoxicillin resistance.

Optionally present in the kit there are also at least one enzyme and at least one buffer, for example enzymes such as DNA polymerase, nucleotides, positive control sequences, negative control sequences, etc.

EXAMPLE

Extraction of Bacterial DNA

About 200 mg of faeces was solubilised in 2 ml of phosphate buffered saline (PBS). Subsequently, the solubilised faeces were homogenised by shaking on a Vortex mixer for about 30 seconds.

Then 500 µl of homogenate was drawn with a sterile syringe and transferred into a new 1.5 ml test tube. 500 µl of Triazol was added to the homogenate, which was vigorously mixed for a few seconds.

Subsequently, 100 µl of chloroform was added to the homogenate-Triazol mixture, which was vigorously mixed for 15 seconds and centrifuged at 12000 g for 15 minutes at 4° C.

This treatment brings about the formation of three distinct phases: an aqueous phase (surface), an interphase (intermediate) and a phenol phase (bottom).

The aqueous phase is discarded.

150 µl of 100% ethanol is added to the remaining phases (interphase and phenol phase), containing the DNA. The sample is mixed by inversion and incubated at room temperature for 2-3 minutes.

Subsequently, the DNA is made to sediment by centrifugation at 2000 g for 2 minutes at 4° C.

Then the surface phase containing protein is removed and 1 ml of sodium citrate is added to the DNA pellet, which is incubated at room temperature for 30 minutes. After this treatment, the sample is centrifuged at 2000 g for 5 minutes at 4° C. and the supernatant is removed.

The sodium citrate step is repeated 2 times;

Then 2 ml of 75% ethanol is added to the pellet, which is incubated for 20 minutes at room temperature and centrifuged at 2000 g for 5 minutes at 4° C. The ethanol is completely removed and the DNA pellet is left to dry for 15-20 minutes.

The DNA pellet is dissolved in 500 µl of 8 mM NaOH. Then the dissolved sample is centrifuged at 14000 g for 10 minutes at room temperature to remove the insoluble material. At the end of the centrifugation step, the supernatant is transferred into a new test tube and the DNA is resuspended in 60 µl of 0.1 M HEPES and 5.5 µl of 100 mM EDTA.

Primary Assembly of the 23S rRNA Sequence of *Helicobacter pylori* (Nucleotide Sequence)

SEQ ID NO: 1 is the nucleotide sequence of the 23S rRNA gene of *Helicobacter pylori*.

This sequence is the site of the point mutations responsible for resistance to clarithromycin.

A genotyping experiment is an end-point experiment used for the determination of the genotype of unknown samples. With this type of experiment it is possible to differentiate a polymorphism due to the mutation of a single nucleotide (SNP), as in the case of *Helicobacter pylori*.

In particular, in the case of resistance to clarithromycin, a genotyping experiment has the aim of determining whether the unknown samples are:

Homozygous for A (samples that have the nucleotide sequence not carrying the mutation)

Homozygous for G (samples that have the nucleotide sequence carrying the mutation)

Heterozygous (samples that have the nucleotide sequence carrying the mutation on one allele and not carrying the mutation on the other allele)

The PCR reactions for the genotyping experiments include the following components:

Negative controls—Specimens containing water or a buffer instead of the sample (also known as no template controls—NTCs). Negative controls should not undergo amplification.

Positive controls—Specimens containing known genotypes.

Sample—the specimen in which the target genotype is not known.

Replicates—Identical reactions containing identical components and volumes.

Genotyping experiments entail two steps:
(i) thermal cycle (PCR amplification); and
(ii) signal end-point detection.

For the genotyping of the mutation on a large scale, the method of real-time PCR with TaqMane® chemistry was used. The target sequence must be preliminarily amplified with suitable primers. The probe, situated between the two primers, identifies the sequence containing the mutation of interest.

Shown below is SEQ ID NO: 2, i.e. the portion of the DNA sequence of the 23S rRNA gene containing the position of the A/G mutation which provokes the clarithromycin resistance of Hp.

The positions of the primers are shown in boldface and the probe is highlighted in grey. As can be seen, the primers straddle the region containing the site of the possible mutation responsible for clarithromycin resistance and the probe is complementary to (i.e. pairs with) a portion of this region precisely where the site of the possible mutation lies.

```
                                              (SEQ ID NO: 24)
TTAAATACCGACCTGCATGAATGGCGAACGAGATGGGAGCTGTCTC

AACCAGAGATTCAGTGAAATTGTAGTGGAGGTGAAAATTCCTCCTA

CCCGCGGC................CCGTGGACCTTTACTACAA

CTTAGCACTGCTAATGGGAATATCATGCGCAGGATAGGTGGGAGGC

TTTGAAGTAAGGGCTTTGGCTCTTATGGAGCCA
```

Thus the primers used for the PCR are the following:

| Primer name | Primer sequence |
|---|---|
| SEQ ID NO: 5 | 5' TCAGTGAAATTGTAGTGGAGGTGAAAA 3' |
| SEQ ID NO: 6 | 5' CAGTGCTAAGTTGTAGTAAAGGTCCA 3' |

The probes used are:

| Probe name | Probe sequence |
|---|---|
| SEQ ID NO: 13 | VIC-AAGACGGAAAGACC-MGB |
| SEQ ID NO: 14 | FAM-CAAGACGGAGAGACCT-MGB |

In particular, the probe marked with the fluorophore VIC was used to discriminate the base A, whilst the probe marked with the fluorophore FAM was used to discriminate the base G (in the case of a mutation).

In a biallelic system, as in the case in question, in the same reaction there are two different probes marked with a different fluorophore (FAM™ for the normal allele and VIC™ for the mutated allele in this case), each complementary to one of the alleles of the SNPs under analysis. During the pairing (annealing) phase, each of the probes will hybridize with its specific strand. The result will be an increase in fluorescence at the specific wavelength of one of the two fluorescent markers (fluorophores) compatible with a state of homozygosity for that given allele, whereas the fluorescence emission at both wavelengths is compatible with a state of heterozygosity.

Generally, allelic discrimination assays are synthesised only if they pass quality control tests:

Each primer and each oligonucleotide probe is individually tested by mass spectroscopy to verify correct synthesis;

At least one easily interpretable allelic discrimination cluster must be produced, i.e. at least one group of units that are similar or close to one another from the standpoint of their composition and/or position; for example, in this case it is a gene cluster or a group of similar or closely correlated products having the same genetic makeup (e.g. a group of samples that exhibit mutated *Helicobacter* p. and/or a group with normal/wild type *Helicobacter* p.);

Assays for which the primers and oligonucleotide probes fail to reach performance standards will not pass the quality control tests;

The sequences alongside the SNPs concerned have been formatted, validated and ordered.

As previously said, in genotyping experiments, PCR includes a specific probe (brief nucleotide sequence including the site of the polymorphism) marked with a fluorescent marker (fluorophore) for each allele. The probes each contain a different high-intensity fluorescent marker (fluorescent reporter) for the purpose of differentiating each allele.

It is possible to use TaqMan® minor groove binder (MGB) probes on the Applied Biosystems 7900HT system in our possession.

Each MGB TaqMan® probe contains:

a fluorochrome reporter at the 5' end of every probe;

In this case the fluorochrome VIC® is bonded to the 5' end of the probe of the wild-type allele;

the fluorochrome FAM™ is bonded to the end 5' of the probe of the mutated allele.

a minor groove binder (MGB).

MGB chemistry increases the melting temperature (Tm) of the probes without increasing their length (Afonina et al., 1997; Kutyavin et al., 1997), thus enabling the design of shorter probes. Accordingly, TaqMan MGB probes show a greater difference in the values of Tm between paired and unpaired probes; greater differences in the values of Tm provide accurate genotyping.

a non-fluorescent quencher (NFQ) at the 3' end of the probe.

In the case in question, the real-time PCR was set up on a 96-well optical reading plate where the following amount of sample was added for each well:

| | |
|---|---|
| TaqMan ® Universal PCR Master Mix | 12.50 μl |
| SNP Genotyping assay | 0.625 μl |
| bdH20 | 9.875 μl |
| DNA | 2.00 μl |

The TaqMan® Universal PCR Master Mix (Applied Biosystems, Foster City, Calif.) contains the buffer, dNTPs and Taq Gold Polymerase.

The SNP Genotyping assay contains the two primers (forward and reverse) and the two probes specific for each allele, one marked at the 5' end with the fluorescent marker FAM™—with red fluorescence—and the other with the fluorescent marker VIC®—with green fluorescence.

The DNA was amplified under the following experimental conditions:

1 min at 60° C. pre-read: to detect the initial emission of fluorescence 2 min at 50° C.

10 min at 95° C.

15 sec at 95° C.

1 min at 60° C. 40 cycles 1 min at 60° C. post-read: to detect the clustering of the three different genotypes.

The results were analysed and read using the SDS software provided.

The sensitivity and specificity of the method were assessed by comparing the aforesaid test with the invasive and non-invasive examinations presently available for the diagnosis of H.p. infection.

A group of patients who were histologically positive for Hp was analysed.

To this end, we compared the aforesaid method with the test presently considered to be the gold standard in the diagnosis of Hp, namely, histological examination, and with DNA extracted from tissue. 72 Hp-positive patients were analysed.

The bacterial DNA was extracted from tissue enclosed in paraffin and subjected to the molecular analysis described above for the identification of the mutation responsible for resistance.

The agreement between the two molecular analyses was 100%.

The agreement with the histological diagnosis was 92%, given the presence of a few false negatives, detectable only by means of molecular analysis.

The comparison between our test and the test for the faecal antigen (Ag) showed 68% agreement.

Therefore, the molecular method of the present invention also enabled identification of the few but significant false negatives resulting from the histological examination and other methods used (faecal Ag).

The frequency of the A2143G mutation was 26%, in line with the data in the literature.

|  | Histology | Fecal antigen | Method of the invention | Mutation A2143G |
|---|---|---|---|---|
| Positive | 66 | 49 | 72 | 19 |
| Negative | 6 | 23 | 0 | 53 |
| Total | 72 | 72 | 72 | 72 |

The invention claimed is:

1. An in vitro method for determining *Helicobacter pylori* (Hp) in a fecal sample isolated from an individual and for determining the resistance of said *Helicobacter pylori* to clarithromycin, said method comprising the steps of:
I. obtaining a fecal sample isolated from the individual;
II. purifying or isolating the DNA from said sample;
III. amplifying SEQ ID NO: 1 or SEQ ID NO: 2 of the 23S rRNA gene of *Helicobacter pylori* comprising at least one mutation site responsible for the resistance to clarithromycin, wherein said at least one mutation site is/are selected from the group consisting of A2143G, A2142C and A2142G, said amplification being performed by real-time PCR using a pair of primers that have the sequences of SEQ ID NO: 5 and SEQ ID NO: 6 and two oligonucleotide probes, where the pair of primers hybridizes in the DNA region straddling said mutation site and where each oligonucleotide probe is marked with a distinguishing marker, and wherein one oligonucleotide probe is complementary and specific to SEQ ID NO: 1 or SEQ ID NO: 2 of the wild-type allele of the 23S rRNA gene and the other oligonucleotide probe is complementary and specific to SEQ ID NO: 1 or SEQ ID NO: 2 of the mutated allele of the 23S rRNA gene responsible for clarithromycin resistance; and
IV. quantifying the amplified wild-type and/or mutated DNA by measuring the levels of the distinguishing markers with which said oligonucleotide probes are marked, where the presence of only the marker with which the probe complementary and specific to SEQ ID NO: 1 or SEQ ID NO: 2 of the wild-type allele is marked defines a normal homozygous genotype and thus the presence of said Hp which is not resistant to clarithromycin; the presence of only the marker with which the probe complementary and specific to SEQ ID NO: 1 or SEQ ID NO: 2 of the mutated allele of the 23S rRNA gene is marked defines a mutated homozygous genotype and hence the presence of said Hp resistant to clarithromycin; and the presence of both markers defines a heterozygous genotype with a wild-type allele and a mutated allele of the 23S rRNA gene, and thus the presence of said Hp resistant to clarithromycin.

2. The method according to claim 1, wherein each oligonucleotide probe is marked at the 5' end with a high-intensity fluorescent marker that functions as a reporter and at the 3' end with a non-fluorescent or low intensity marker that functions as a quencher.

3. The method according to claim 1, wherein the distinguishing markers are selected from the group consisting of VIC, FAM, HEX, JOE, NED, SYBER, TAMRA, TET and ROX.

4. The method according to claim 1, wherein said at least one mutation site comprises a point mutation or a single nucleotide polymorphism (SNP).

5. The method according to claim 1, wherein one or both of said oligonucleotide probes are modified with minor groove binder chemistry.

6. The method according to claim 1, wherein said two oligonucleotide probes are SEQ ID NO: 13 and 14, wherein SEQ ID NO: 13 is complementary to SEQ ID NO: 1 or SEQ ID NO: 2 of the 23S rRNA gene without the mutation responsible for antibiotic resistance; and SEQ ID NO: 14 being complementary to SEQ ID NO: 1 or SEQ ID NO: 2 of the 23S rRNA gene with a mutation responsible for clarithromycin resistance, selected from the group consisting of A2143G, A2142C and A2142G.

7. A kit for determining *Helicobacter pylori* in a fecal sample isolated from an individual and for determining the resistance of said *Helicobacter pylori* to clarithromycin caused by a mutation of the 23S rRNA gene selected from the group consisting of A2143G, A2142C and A2142G; said kit comprising:
a pair of primers for amplifying, by real-time PCR, at least one portion of at least one *Helicobacter pylori* gene comprising at least one mutation site responsible for the resistance to clarithromycin, wherein said pair of primers are SEQ ID NO: 5 and 6; and
two marked oligonucleotide probes, wherein each oligonucleotide probe is marked with a distinguishing marker, wherein one oligonucleotide probe is complementary and specific to at least one portion of a wild-type allele of at least one gene of *Helicobacter pylori* comprising at least one mutation site responsible for the resistance to clarithromycin and the other oligonucleotide probe is complementary and specific to at least one portion of a mutated allele of at least one gene of *Helicobacter pylori* comprising at least one mutation site responsible for the resistance to clarithromycin, wherein said oligonucleotide probes are SEQ ID NO: 13 and SEQ ID NO: 14, wherein SEQ ID NO: 13 is complementary to at least one portion of the 23S rRNA gene without the mutation responsible for clarithromycin resistance; and SEQ ID NO: 14 is complementary to at least one portion of the 23S rRNA gene with a mutation responsible for clarithromycin resistance, selected from the group consisting of A2143G, A2142C and A2142G.

\* \* \* \* \*